United States Patent [19]

Bellak

[11] Patent Number: 4,895,140

[45] Date of Patent: Jan. 23, 1990

[54] DEVICE FOR OVERCOMING MALE DYSFUNCTION OR IMPOTENCE

[75] Inventor: Leopold Bellak, Larchmont, N.Y.

[73] Assignee: C.P.S. Inc., Larchmont, N.Y.

[21] Appl. No.: 229,630

[22] Filed: Aug. 8, 1988

[51] Int. Cl.$^4$ .............................................. A61F 5/00
[52] U.S. Cl. .................................................... 128/79
[58] Field of Search ...................... 128/79 A, 842, 843, 128/844, 79; 623/11; 2/21; 139/383 R, 383 B, 385.5, 387 R, 389; 87/6, 7, 8, 9; 604/349–353

[56] References Cited

U.S. PATENT DOCUMENTS

| | | | |
|---|---|---|---|
| 3,608,552 | 9/1971 | Broerman | 604/349 |
| 3,939,827 | 2/1976 | Brunstetter | 128/79 |
| 3,998,228 | 12/1976 | Poidomani | 604/349 |
| 4,564,006 | 1/1986 | Pomeranz | 604/349 |
| 4,777,859 | 10/1988 | Plummer Jr. | 139/387 R |

Primary Examiner—Robert A. Hafer
Assistant Examiner—Charles H. Sam
Attorney, Agent, or Firm—Herbert Dubno

[57] ABSTRACT

A sheath for stiffening the penis to overcome male dysfunction and sexual impotence comprises circular and longitudinal filaments which are interwoven with one another and with crossing filaments so that the sheath can be unrolled along the penis and rolled up again and, when unrolled, is sufficiently stiff to rigidify the penis for the sex act. The crossing filaments form a braid which like Chinese novelty handcuffs or finger-cuffs stiffen as tension is applied to the sheath.

6 Claims, 1 Drawing Sheet

DEVICE FOR OVERCOMING MALE DYSFUNCTION OR IMPOTENCE

FIELD OF THE INVENTION

My present invention relates to a device for overcoming male dysfunction or impotence and, more particularly, to a device which can be applied to the penis of a user to hold the penis erect for the performance of sexual intercourse. The invention also relates to a device which is capable of overcoming the problem of male dysfunction or impotence, does not require implantation and also is capable of preventing contamination or use as a contraceptive measure.

BACKGROUND OF THE INVENTION

While the problem of male dysfunction or impotence is age-old, the approaches used heretofore to overcome the problem of a flaccid penis in intercourse have concentrated largely upon implanted prosthetic devices and devices which are applied to the penis but use fluids to inflate or stiffen the device. For example, in U.S. Pat. No. 4,399,812 a prosthetic device is described for implantation within the penis that has a pumping mechanism integral and in fluid communication with a fluid storage reservoir. Fluid is pumped manually to an expandable portion of the device which renders the penis rigid and capable of sexual activity. With relaxation of the penis when desired, the fluid is permitted to flow back into the storage section.

Another prosthetic device is described in U.S. Pat. No. 4,318,396.

In U.S. Pat. No. 4,349,026, the regenerated fiber collagen condom is described utilizing fiber collagen which is cross-linked. A method of making this condom is likewise taught. However, while the condom appears to have significant strength, there is no indication that it can assist in the problem of male dysfunction or sexual impotence. A condom of this type is likewise described in U.S. Pat. No. 4,406,853.

U.S. Pat. No. 4,354,494 describes a condom having a retention strap. There is no teaching here that this device is capable of providing a solution in whole or in part to the problem of male dysfunction or impotence.

U.S. Pat. No. 4,224,933 describes a sexual stabilizer and stimulator worn on a penis for exciting both partners of a sex act. This device comprises a tubular sleeve of thin latex having constrictions at opposite ends thereof and stiffening stays embedded in the sleeve extending longitudinally. A zigzag row of balls is tethered on the outer side of the sleeve. The stays assist in maintaining the penis erect.

The implantation type of prosthesis is described in U.S. Pat. No. 4,177,805 and has an encasing body in which a stiffening bar is embedded. A joint is provided allowing bending of the implant in only one direction so that the device is of the two-position type, having a straddled position facilitating the performance of the sex act and a curved position for ordinary inactive orientation of the penis.

Mention may also be made of U.S. Pat. No. 3,744,486 which also refers to an apparatus for obtaining an artificial erection and to a number of patents in which rheopexic material is used so that the condom stiffens in use. The latter patents include U.S. Pat. Nos. 4,4321,357, 4,498,466 and 4,564,006.

U.S. Pat. No. 4,527,988 describes a condom provided with a large number of small holes to allow the transfer of biological fluids other than but preventing the passage of spermatozoa.

With the exception of the patent described above which provides stays in a condom to provide a stiffening effect during intercourse, the approach in the past, therefore, has largely involved the use of rheopexic materials, pumped fluids and implants to achieve the penile stiffening which is required for intercourse.

These devices have obvious disadvantages. Implants, for example, require surgical intervention and pumped devices generally require a series of manipulations which may not always lead to a satisfactory degree of stiffening.

While a condom with stiffening stays may provide a satisfactory result, in many cases it is not desirable to cover the glans and thereby reduce the sexual stimulation effect.

OBJECTS OF THE INVENTION

It is, therefore, the principal object of the present invention to provide a sheath for a flaccid penis which can erect or rigidify the penis without surgical intervention or a fluid pumping-action so as to overcome the problem of male dysfunction or sexual impotence.

It is another object of my invention to provide a device for the purposes described which will overcome, at least in part, the problem of male dysfunction or sexual impotence without the drawbacks of some or all of the prior art approaches discussed above.

The present invention comprises a sheath consisting of circular, longitudinal and crossing or braided fibers which can be rolled up and then unrolled along the penis to provide a stiffening structure capable of retaining the penis in an erect or rigid configuration.

The braided or crossing fibers can resemble the novelty items widely disseminated in earlier years and into which one can place one fingers and which thereupon lock the fingers when traction is applied to the device, such devices being known variously as Chinese torture, Chinese handcuffs or Chinese finger-cuffs.

The advantage of the device of the invention is that the fibers can be extremely thin, i.e. of small diameter so that they do not serve to impede sensitivity, especially when the glans of the penis is left uncovered, but may even form a textured surface along the length of the penis for stimulating the other party to the sex act.

The device may be applied as a reinforcement to a latex or like condom, if desired.

The device of the invention mimics largely, by its arrangement of circular fibers and longitudinal fibers, the structure of the muscle fibers in the vagina. For removal, the device may be simply rolled off.

BRIEF DESCRIPTION OF THE DRAWINGS

The above and other objects, features and advantages of the present invention will become more readily apparent from the following description, reference being made to the accompanying drawing in which.

SPECIFIC DESCRIPTION

Figure 1:
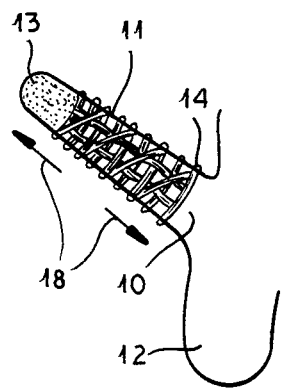
FIG. 1 is a diagrammatic elevational view showing the device of the invention applied to support a flaccid penis and hold the same erect.

As can be seen in FIG. 1, a penis 10 of an individual may be provided, according to the invention, with a sheath 11 which can extend from the junction of the penis with the scrotum 12 to a point just behind the glans 13.

The sheath is provided in a roll and is sufficiently flexible to allow it to be rolled over the penis from a base ring 14 of the sheath which can be thicker than the other filaments thereof.

Figure 2:
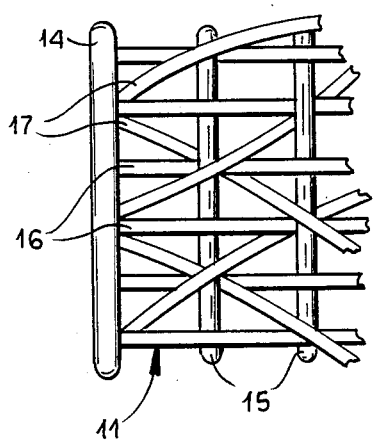
FIG. 2 is a detail of the woven construction of the device.

As can be seen from FIG. 2, the sheath 11 can consist of spaced-apart circular rings 15 of the filament, e.g. a synthetic resin monofilament such as a polyester-like polyethylenetetraphthalate. The longitudinal filaments 16 which are interwoven with the circular or transverse filaments 15 are likewise composed of such monofilament in a preferred embodiment of the invention and may be ultrasonically bonded or tacked at the crossover points with the circular filaments to form an easily rollable structure which is quite stiff when unrolled to its cylindrical configuration. However, such tacking is by no means necessary.

In addition, the sheath may be formed with helical filaments 17 extending in opposite senses around the sheath and interwoven with one another and with the longitudinal and transverse filaments to form a braid with one another so that these filaments can act like the strands of the Chinese finger-cuff or handcuff novelty to stiffen the sheath when tension is applied thereto during the sex act. The braid filaments 17 are not tacked to the longitudinal or transverse filaments and thus can flex and shift as is necessary for the stiffening action upon elongation of the cylinder as represented by the arrows 18 in FIG. 1. As can be seen from FIG. 1, moreover, the glans 13 is uncovered and thus the sensitivity of the penis for the purposes of sexual stimulation is unimpeded by the stiffening device of the invention.

However, if the filaments themselves are sufficiently thin, they may be woven to form a basket encasing the glans of the penis if desired. This facilitates extension of the sheath and hence the stiffening effect brought about by constriction of the braid. The filaments should be so thin that at least the longitudinal filaments are somewhat extensible by plastic deformation.

The device, of course, may be disposable and is removed by rerolling after the tube has been relaxed on the penis by urging the base ring 14 toward the tip of the penis or pressing the distal end of the sheath toward the ring 14.

Figure 3:
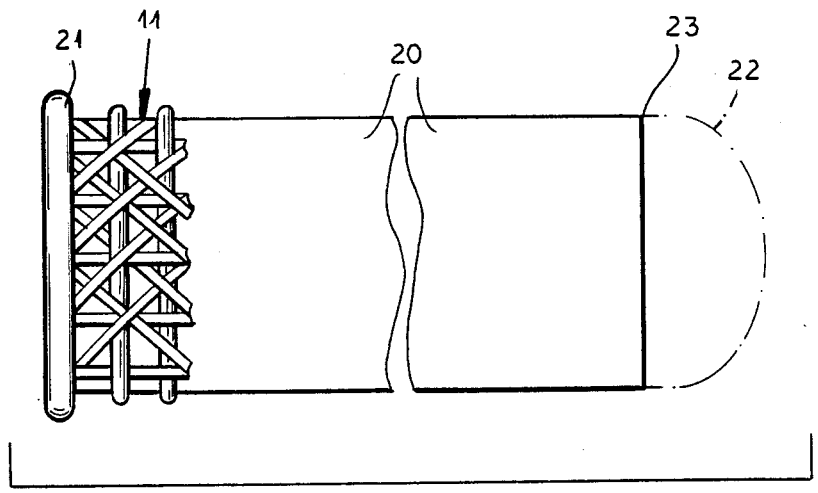
FIG. 3 is a diagrammatic elevation showing the device as applied to a latex sheath which may form a condom, if desired.

In FIG. 3, I have shown an arrangement in which the sheath 11 is applied to the exterior of a latex condom 20 having a rolling ring 21 at one end. The condom may be closed at 22 at its opposite end if it is to be used as protection against contamination by AIDS or other sexually-transmitted diseases, or for contraceptive purposes.

It is possible, however, to provide a latex sheath as an inner liner for the sheath 11 and to terminate it at 23 when the glans of the penis are to remain exposed.

The device, of course, provides a unique external texture which consists in stimulating the sexual partner. Preferably the filaments have diameters no greater than about 1 mm and can range in diameter from say 0.1 mm to 1 mm.

I claim:

1. A device for overcoming male dysfunction and sexual impotence which comprises a flexible woven stiffening sheath adapted to be unrolled along the penis and consisting of interwoven longitudinal and circular filaments, and mutually crossing filaments crossing said longitudinal and circular filaments and interwoven with said longitudinal and circular filaments to form a braid with one another.

2. The device defined in claim 1, further comprising a latex sheath lining said stiffening sheath.

3. Te device defined in claim 2 wherein said latex sheath forms a condom and is closed at one end.

4. A method of at least partly overcoming male dysfunction and sexual impotence which comprises the step of applying to the penis of a male subject suffering from an inability to maintain an erection, a flexible woven stiffening sheath by unrolling it along the penis and consists of interwoven longitudinal and circular filaments, and mutually crossing filaments crossing said longitudinal and circular filaments and interwoven with said longitudinal and circular filaments and forming a braid with one another.

5. The method defined in claim 4 wherein said stiffening sheath is lined with a latex sheath.

6. The method defined in claim 5 wherein said latex sheath forms a condom and is closed at one end.

* * * * *